United States Patent

Ball

[11] Patent Number: 6,139,488
[45] Date of Patent: Oct. 31, 2000

[54] BIASING DEVICE FOR IMPLANTABLE HEARING DEVICES

[75] Inventor: Geoffrey R. Ball, Sunnyvale, Calif.

[73] Assignee: Symphonix Devices, Inc., San Jose, Calif.

[21] Appl. No.: 09/145,374

[22] Filed: Sep. 1, 1998

Related U.S. Application Data

[60] Provisional application No. 60/059,966, Sep. 25, 1997.

[51] Int. Cl.[7] .................................................. H04R 25/00
[52] U.S. Cl. .............................................................. 600/25
[58] Field of Search ........................ 600/25; 607/55–57; 181/126, 129–30, 134–35; 381/69

[56] References Cited

U.S. PATENT DOCUMENTS

| | | | |
|---|---|---|---|
| 3,870,832 | 3/1975 | Frederickson | 179/107 |
| 4,625,137 | 11/1986 | Tomono | 310/317 |
| 4,729,366 | 3/1988 | Schaefer | 128/1.6 |
| 4,850,962 | 7/1989 | Schaefer | 600/25 |
| 5,015,224 | 5/1991 | Maniglia | 600/25 |
| 5,061,280 | 10/1991 | Prescott | 623/10 |
| 5,498,226 | 3/1996 | Lenkauskas | 600/25 |
| 5,531,787 | 7/1996 | Lesinski et al. | 623/10 |

FOREIGN PATENT DOCUMENTS

| | | | |
|---|---|---|---|
| 563 767 A1 | 10/1993 | European Pat. Off. | A61F 2/18 |
| WO90/07915 | 7/1990 | WIPO | A61F 2/18 |

OTHER PUBLICATIONS

T. Ohno et al., Performance of the Middel Ear Implants, (1988) Adv. Audiol. vol. 4, pp. 85–96.

Mechanical Springs, (1989), *Mechanical Engineering Design*, pp. 413–449.

R. Goode et al., Measurement of Umbo and TM Vibration in Human Subjects—Methods and Possible Clinical Applications, 10 pages.

*Primary Examiner*—John P. Lacyk
*Attorney, Agent, or Firm*—Townsend and Townsend and Crew LLP

[57] ABSTRACT

An implantable hearing device is coupled to a tympanic membrane and an oval window of a human subject's ear. The implantable hearing device includes an amplifier, a first transducer electrically coupled to the amplifier, and a second transducer also electrically coupled to the amplifier. A first compliant connecting member elastically couples the tympanic membrane to the first transducer. A second compliant connecting member elastically couples the second transducer to the oval window. Ambient sounds are transmitted from the tympanic membrane to the first transducer by the first compliant connecting member, thus generating an audio signal. The audio signal is amplified by the amplifier, which drives the second transducer. The second compliant connecting member transmits the amplified sounds to the oval window, possibly via one or more ossicles or prostheses. The hearing of the human subject is thus improved.

26 Claims, 12 Drawing Sheets

BIASING DEVICE FOR IMPLANTABLE HEARING DEVICES

This application is a continuation-in-part of and claims the benefit of U.S. application Ser. No. 60/059,966, filed Sep. 25, 1997, the disclosure of which is incorporated by reference.

BACKGROUND OF THE INVENTION

The present invention relates to a method and apparatus for improving the impaired hearing of a human subject using an implantable hearing aid device. More specifically, the present invention relates to a method and apparatus for improving the performance of implantable hearing aid devices.

The human hearing mechanism is a complex system of levers, membranes, fluid reservoirs, neurons, and hair cells which must work in concert to deliver nervous stimuli to the brain where this information is compiled into what we perceive as sound. Because the human hearing system encompasses a complicated mix of acoustic, mechanical, and neurological systems, there is ample opportunity for its impairment. Unfortunately, this is often the case.

Attempts to remedy such deficiencies have a long history. The first electronic hearing aids began making their debut in the early 1900's. The development of the transistor led to smaller, more power-efficient aids that began to appear in the 1950's. In the 1960's and 70's, the hearing aid enjoyed a period of accelerated development.

The hearing impaired patient now has a wide variety of hearing devices to choose from. Devices having improved circuits, now permit a hearing aid's frequency response to be customized to a patient's individual hearing loss. New devices located completely in the patient's ear canal are available that are cosmetically superior to the large, bulky devices of years past.

Figure 1:
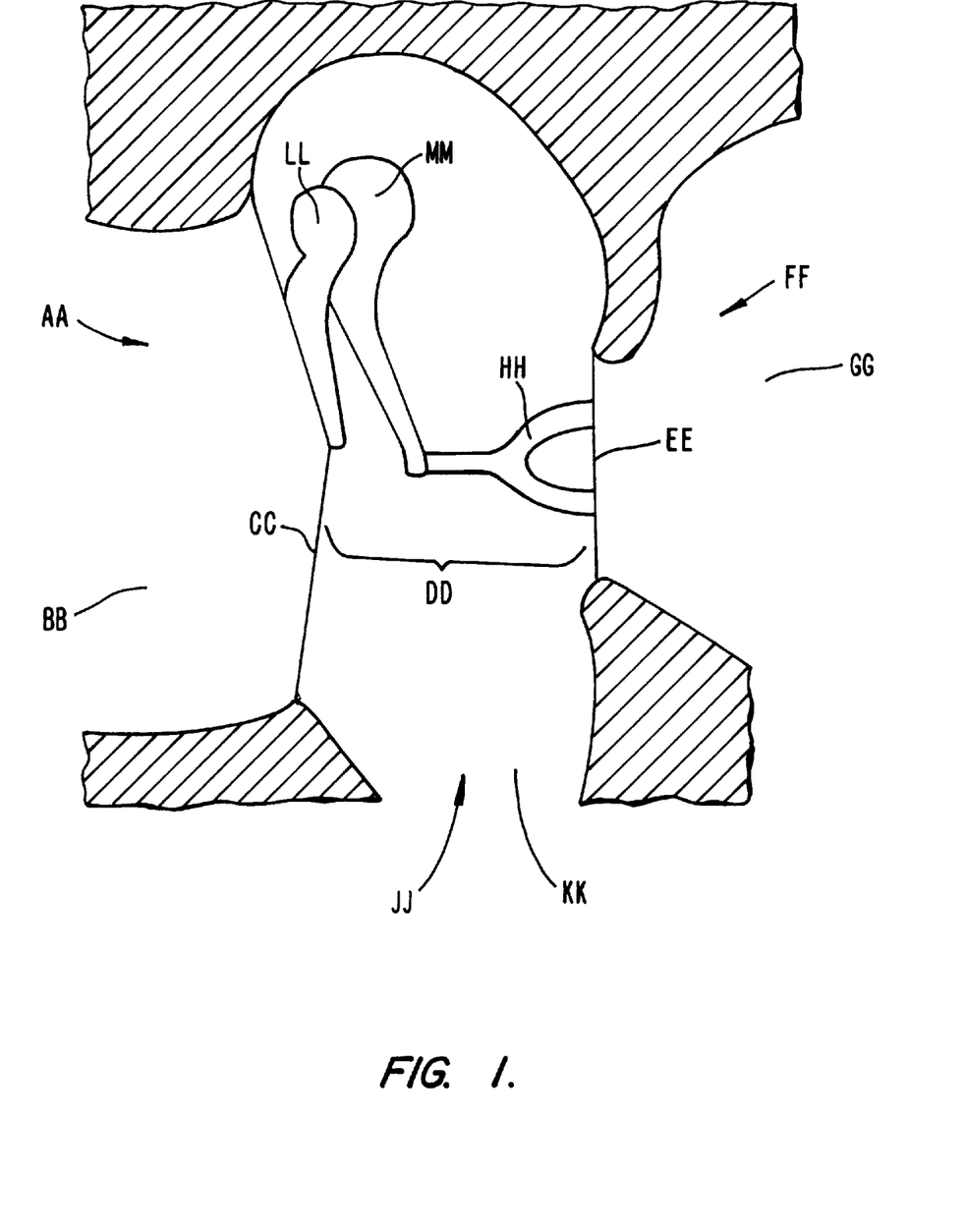
FIG. 1 is a schematic section through a portion of the skull of a human subject showing certain of the elements of the human ear.

A number of auditory system defects are now known to impair or prevent hearing. To illustrate such defects, a schematic representation of part of the human auditory system is shown in FIG. 1. The auditory system is generally comprised of an external ear AA, a middle ear JJ, and an internal ear FF. External ear AA includes ear canal BB and tympanic membrane CC, and internal ear FF includes an oval window EE and a vestibule GG (a passageway to the cochlea (not shown)). Middle ear JJ is positioned between external ear AA and internal ear FF, and includes eustachian tube KK and three bones called ossicles DD. Ossicles DD include a malleus LL, an incus MM, and a stapes HH, which are positioned between and connected to tympanic membrane CC and oval window EE.

In a person with normal hearing, sound enters the external ear AA where it is slightly amplified by the resonant characteristics of ear canal BB. The sound waves produce vibrations in tympanic membrane CC, the part of external ear AA that is positioned at the distal end of ear canal BB. The force of these vibrations is magnified by ossicles DD.

Upon vibration of ossicles DD, oval window EE, which is part of internal ear FF, conducts the vibrations to cochlear fluid (not shown) in inner ear FF thereby stimulating receptor cells, or hairs, within the cochlea (not shown). Vibrations in the cochlear fluid also conduct vibrations to the round window (not shown). In response to the stimulation, the hairs generate an electrochemical signal which is delivered to the brain via one of the cranial nerves, causing the brain to perceive sound.

The vibratory structures of the ear include the tympanic membrane, ossicles (malleus, incus, and stapes), oval window, round window, and cochlea. Each of the vibratory structures of the ear vibrates to some degree when a person with normal hearing hears sound waves. However, hearing loss in a person may be evidenced by one or more vibratory structures vibrating less than normal or not at all. Some patients with hearing loss have ossicles that lack the resiliency necessary to increase the force of vibrations to a level that will adequately stimulate the receptor cells in the cochlea. Other patients have ossicles that are broken, and which therefore do not conduct sound vibrations to the oval window.

Various types of hearing aids have been developed to restore or improve hearing for the hearing impaired. With conventional hearing aids, sound is detected by a microphone, amplified using amplification circuitry, and transmitted in the form of acoustical energy by a speaker or another type of transducer into the middle ear by way of the tympanic membrane. Often, the acoustical energy delivered by the speaker is detected by the microphone, causing a high-pitched feedback whistle. Moreover, the amplified sound produced by conventional hearing aids normally includes a significant amount of distortion.

An interesting implementation concerns implantable hearing aids configured for disposition principally within the middle ear space. For example, such an approach could provide a transducer capable of converting mechanical vibration within the ossicular chain into an output voltage (e.g., a piezoelectric transducer). That output voltage could be converted to mechanical vibrations (e.g., again, by a piezoelectric transducer) and applied to the area of the oval window to stimulate it. Alternatively, the output voltage could be used to electrically stimulate the auditory nerve. As an alternative, the stapes may be removed and the hearing aid physically located in its stead, conditions permitting. Under circumstances where the stapes is removed, the end of the incus is free-standing and the hearing aid may be physically associated with it, such as by means of crimpable rings or the like. Thus the hearing aid serves as an integral part of the mechanical linkage in the transmission of forces from the eardrum to the oval window in all events, whether or not the integrity or continuity of the ossicular chain remains unimpaired. That being the case, however, unwanted mechanical feedback through the ossicular chain is a possibility, diminishing the overall efficacy of this approach.

Methods have been devised to avoid this unwanted feedback, and so improve the hearing of patients using such devices. For example, such an invention is described in "IMPLANTABLE HEARING AID AND METHOD OF IMPROVING HEARING" by D. W. Schaefer (U.S. Pat. No. 4,729,366), which is hereby incorporated by reference in its entirety. Schaefer describes a method and apparatus for improving the impaired hearing of a subject utilizing a device which receives vibrations from one of the subject's ossicles or the subject's eardrum, and provides an amplified version of those vibrations to the subject's inner ear.

Figure 2:
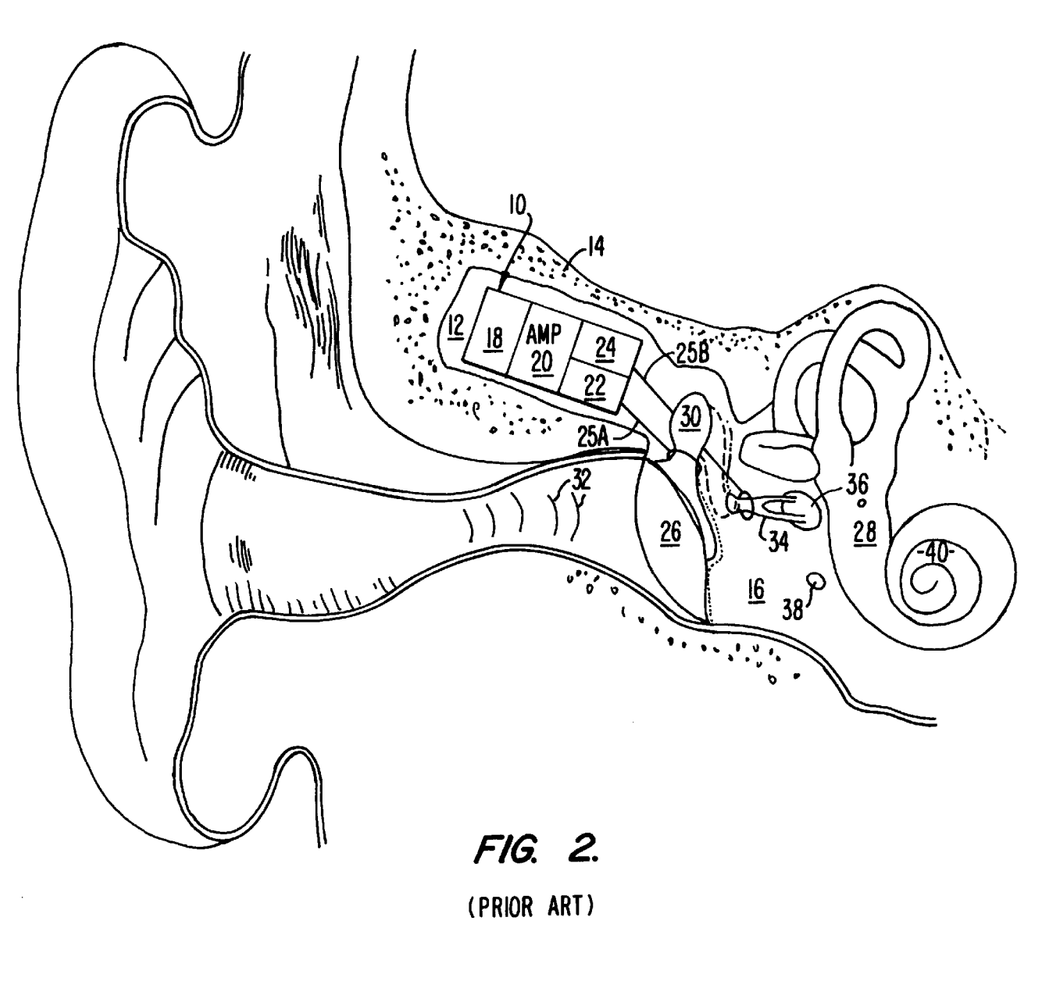
FIG. 2 is a schematic section through a portion of the skull of a human subject adjacent to the ear showing the disposition of an implantable hearing aid of the prior art.

Referring to FIG. 2, one embodiment of an implantable hearing device 10 according to Schaefer is shown disposed in an antrum 12 surgically developed in the mastoid bone of a subject's skull 14. Antrum 12 communicates with a middle ear space 16 of the subject. Device 10 may include, for example, a power source 18, an amplifier 20, an input transducer 22, and an output transducer 24. Input transducer 22 converts mechanical vibrations to electrical signals, while output transducer 24 converts electrical signals to mechanical vibrations.

Input transducer 22 and output transducer 24 may, for example, each include a piezoelectric element cooperating with a resilient diaphragm. A connecting member 25, mounted on a diaphragm (not shown), is operatively coupled to piezoelectric element (also not shown). Schaefer indicates that connecting member 25 is preferably a rigid stainless steel wire. (The respective connecting members 25 associated with input transducer 22 and output transducer 24 will be referenced as wires 25A and 25B, respectively.)

Input transducer 22 converts vibrations of a tympanic membrane 26 into electrical signals. Input transducer 22 is mechanically coupled to tympanic membrane 26 by wire 25A to a malleus 30 of the subject. Wire 25A must have an acceptable degree of stiffness and may be affixed to malleus 30 utilizing surgical techniques similar to those used in ossicular reconstructive surgery, for example. Tympanic membrane 26 vibrates in response to sound waves 32. The vibrations are transmitted to malleus 30, through wire 25A to input transducer 22. These vibrations are converted to electrical signals by a first piezoelectric element within input transducer 22 (not shown). The electrical signals are then applied to amplifier 20. Amplifier 20 amplifies these input signals in a manner sufficient to drive output transducer 24, compensating for deficiencies in the frequency response of the subject's hearing.

Output transducer 24 converts the amplified electrical signals representing the tympanic vibrations into mechanical vibrations for application to an inner ear 28 of the subject. The amplified electrical signals are converted into corresponding mechanical vibrations by a second piezoelectric element within output transducer 24 (also not shown). The vibrations are communicated to inner ear 28 by a mechanical connection between wire 25B and a stapes 34. Stapes 34 then transmits these vibrations to an oval window 36 of inner ear 28. In this manner, the vibrations are transmitted to a cochlea 40 of the subject. The connection between wire 25B and inner ear 28 can be made in a manner similar to techniques employed in reconstructive surgery using passive mechanical prosthetic devices, for example.

Implantable hearing devices such as those in Schaefer have been used with the ossicular chain intact. However, Schaefer prefers that the ossicular chain be broken to prevent positive feedback of the amplified vibrations to input transducer 22 (e.g., via the incus). A break would typically be effected by removing at least one of the component parts of the ossicular chain, typically the incus. It is desirable to maintain the malleus and stapes in normal anatomical position with muscle and tendon intact to maintain the subject's natural defense mechanism against acoustic trauma. The hearing aid then becomes an integral piece of the ossicular chain.

As noted, wires 25A and 25B are preferably made of a substantially rigid material such as stainless steel. Such materials are used in the interest of accurately transmitting the mechanical vibrations correspond to sound waves 32, thereby providing faithful reproduction of the sounds received at the eardrum. Schaefer discusses several methods of attaching the distal ends of these wires to the ossicles or other structures.

For an implantable hearing aid such as that described in Schaefer to provide acceptable fidelity over the long term, however, the tension on the wires used to input and output mechanical vibrations preferably remains constant. While a simple attachment, such as is described in Schaefer, may provide acceptable performance in the near term, aging of the various auditory structures involved may cause these attachments to loosen or otherwise cause wires 25A and 25B to lose tension, impairing the hearing aid's performance.

SUMMARY OF THE INVENTION

The present invention solves at least some of the problems associated with the prior art by providing an improved implantable hearing device that employs one or more connecting members adapted to elastically couple the device to a component or else between components of the middle ear. The coupling preferably maintains a tensive (or compressive) force on mechanical couplings between the hearing device and structures of the subject's ear. Use of such connecting members at least partly accommodates post-implantation changes in the positional relationship between the hearing device and the subject's anatomy, which in the absence of the coupling, would impair the fidelity of sound reproduction. Such positional changes may be due to aging (of either the hearing aid or the auditory structures), changes in pressure (e.g., scuba diving or flying in an airplane), physical forces (e.g., a helmet or motion of the subject's head), and other reasons. Tension provided by a connecting member may also maintain the dampening necessary for acceptable sound reproduction over the long term. A tympanic membrane which is not dampened or is poorly dampened will have an increased probability of delivering erratic or distorted mechanical stimuli to the hearing aid's input transducer.

The connecting member of the present invention comprises an elastic (extensible and/or compressible) mechanism or material, and so is described as being "compliant," the term being further defined below.

The desired adaptability and dampening can be achieved by positioning one or more compliant connecting members at any point or points within the mechanical linkage between the native components of the ear.

In one embodiment, an implantable hearing device is described, which is adapted to being coupled between a tympanic membrane and an oval window of a human subject's ear. The implantable hearing device includes an amplifier, a first transducer electrically coupled to the amplifier, and a second transducer also electrically coupled to the amplifier. A first compliant connecting member is capable of elastically coupling the tympanic membrane to the first transducer. A second compliant connecting member is capable of elastically coupling the second transducer to the oval window. The compliant connecting members may be, for example, springs or urethane strips. Ambient sounds are transmitted from the tympanic membrane to the first transducer by the first compliant connecting member, thus generating an audio signal. The audio signal is amplified by the amplifier, which drives the second transducer. The second compliant connecting member transmits the amplified sounds from the second transducer to the oval window, optionally via one or more ossicles or prostheses.

In another embodiment, an implantable hearing device, adapted to couple one or more ossicles of an inner ear of a human subject, includes a housing and an electromagnetic unit. The electromagnetic unit includes a magnet, disposed inside the housing, and a coil, surrounding a portion of the housing. A diaphragm is mechanically coupled to the electromagnetic unit. The motion of the diaphragm is proportional to movement of the magnet caused by an electrical signal applied to the electromagnetic unit. A compliant connecting member elastically couples the diaphragm to one or more ossicles of the human ear. The diaphragm is preferred since it can capture the mechanical energy of the magnet, and evenly translate the mechanical motion of the magnet to the connecting member, regardless of the internal geometry of the electromagnetic unit or the shape of the magnet.

In yet another embodiment, an implantable hearing device, adapted to be coupled to one or more ossicles of an inner ear of a human subject, includes a coil and a compliant connecting member. The compliant coupling member elastically couples the coil to a magnet. The magnet is, in turn, coupled to one or more ossicles of the human ear. The coil, when electrically driven by signals applied thereto, induces a motion in the magnet. The magnet responds in proportion to the applied signals and causes movement to one or more ossicles of the inner ear.

In another aspect of the invention, a method of improving hearing in a human subject using an improved implantable hearing device coupled to a component of an ear of the human subject is described. The method includes implanting an implantable hearing device into a mastoid bone of the human subject and elastically coupling the implantable hearing device to the component of the ear usually using a compliant connecting member. By providing tensive (or compressive) force, the compliant connecting member maintains consistent connection between the implantable hearing device and the component of the ear.

In yet another aspect of the invention, a method of improving hearing in a human subject, where an ear of the human subject has a middle ear structure, comprises implanting an implantable hearing device in a mastoid bone of the human subject. The implantable hearing device includes an electromagnetic unit having a diaphragm which is mechanically driven by the electromagnetic unit. The method also includes elastically coupling the diaphragm to a component of the middle ear structure, using a compliant connecting member.

In yet another aspect of the present invention, a method of improving hearing in a human subject where the human subject has an ear with a middle ear structure is described. The method includes implanting a magnet on a component of the middle ear structure; elastically coupling the magnet to a first portion of a compliant connecting member; and elastically coupling a coil device to a second portion of the compliant connecting member.

A further understanding of the nature and advantages of the present invention may be realized by reference to the remaining portions of the specification and the drawings.

DESCRIPTION OF THE PREFERRED EMBODIMENT

Figure 3:
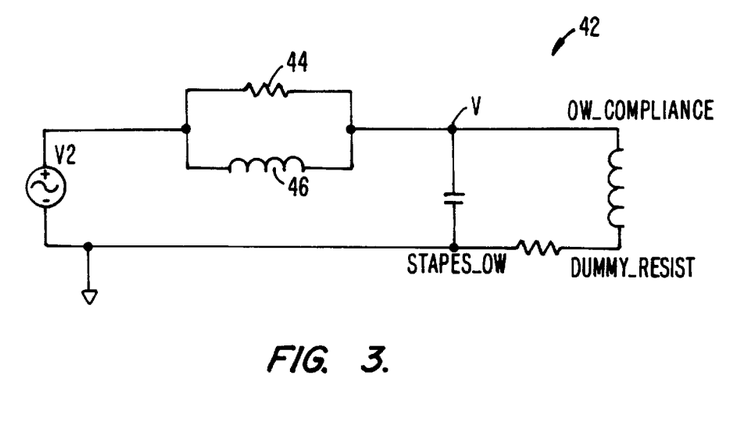
FIG. 3 is a schematic model of a compliant connecting member according to the present invention.
Figure 3A:
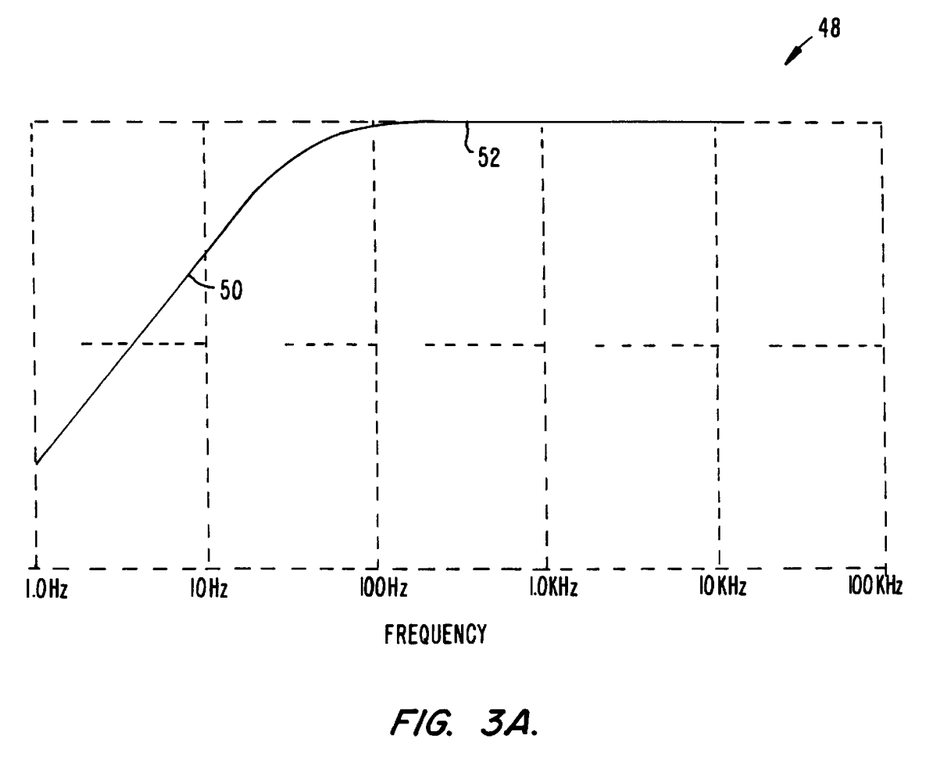
FIG. 3A is a graphical representation of the response of the system as modeled in FIG. 3.

As used herein, a "compliant" connecting member transmits acoustic energy above 100 Hz, such that the acoustic signal is not significantly degraded. At the same time, the compliant connecting member provides a constant bias on to the component or components to which it may be attached, allowing for small displacements that may occur, for example, during shifting. As can be better understood from FIG. 3, the compliant connecting member of the present invention, by way of example, can be modeled as a mechanical circuit 42. The compliant connecting member is made to combine in series the physical properties of a resistance or damper 44 (viscous) and a spring 46 (elasticity). Thus, as illustrated in graph 48 of FIG. 3A, the compliant connecting member responds by compensating for relatively slow physical movements (i.e., have relatively high dampening at low frequencies) 50, while transmitting audible vibrations that are relatively high in frequency (i.e., have relatively low dampening at audio frequencies) 52. Acceptable sound reproduction is thus maintained.

The spring force in the compliant connecting member is determined using clinical data. In any event, the magnitude of the spring force is low enough to avoid damaging the components to which it is attached or other items which may be connected to the component. Also, the spring force does not alter the acoustic characteristics of the outer, middle, or inner ear.

After determining the spring force, the resistance value is tuned such that the system as a whole has the desired characteristic of transmitting a complete signal above 100 Hz. At frequencies below 100 Hz the signal drops off steeply in magnitude. In one example, when the spring force is equal to 1 N/m, the resistance value may be as high as 100 N/m.

This set of properties for the compliant connecting member can be, but are not limited to, being created through a combination of various material properties, material shapes, and/or mechanical components.

Figure 4:
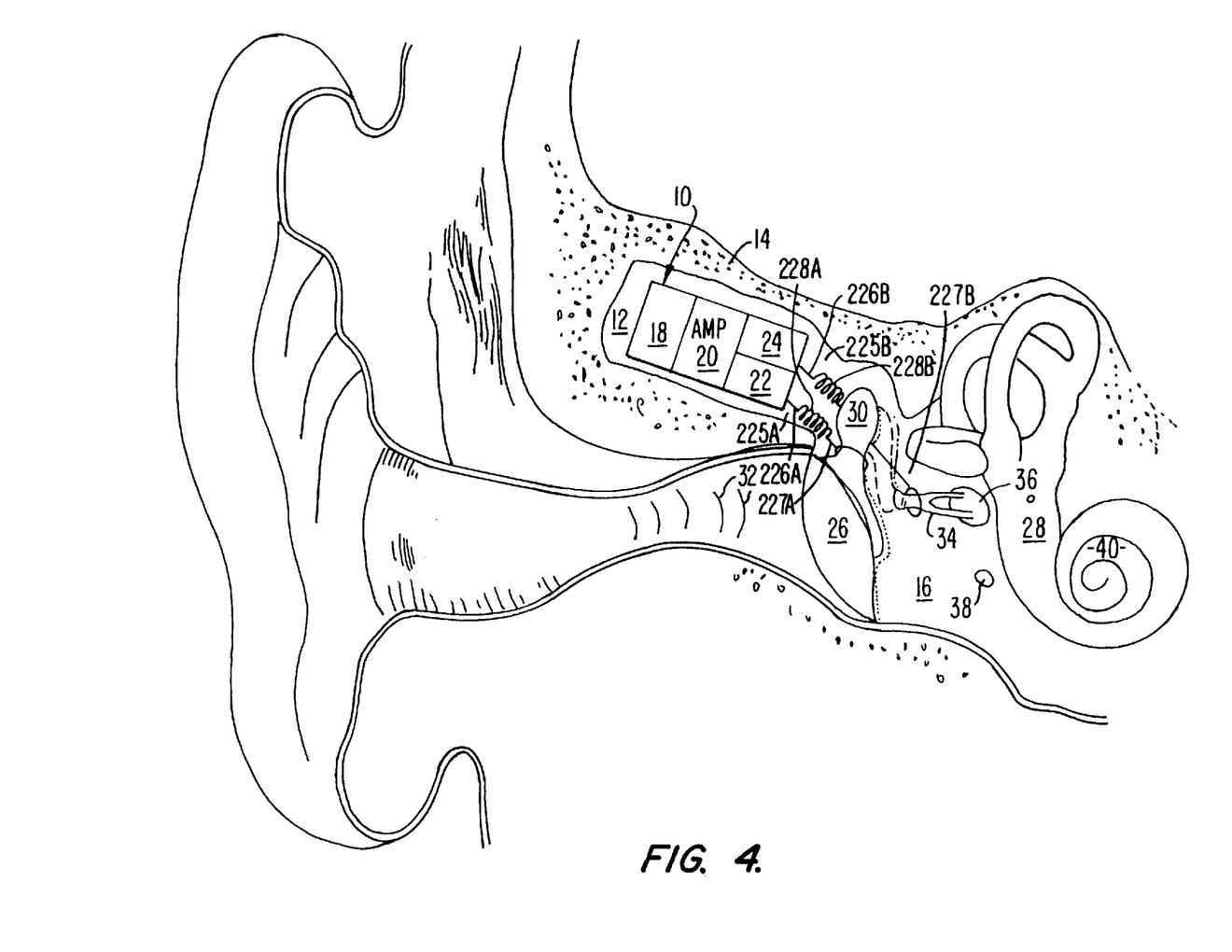
FIG. 4 is a schematic section through a portion of the skull of a human subject an implantable hearing aid according to one embodiment of the present invention.

FIG. 4 illustrates implantable hearing device 10 having improvements according to the present invention. According to the present invention, wires 25A and 25B are replaced with compliant connecting members 225A and 225B. Compliant connecting members 225A and 225B are shown in FIG. 4 as including springs 228A and 228B. Spring 228A is connected to input transducer 22 by a connecting wire 226A and to malleus 30 by a connecting wire 227A. Spring 228B is connected to output transducer 24 by a connecting wire 226B and to stapes 34 by a connecting wire 227B. Preferably, compliant connecting members 225A and 225B are each fabricated from a single wire, but may also be constructed from separate parts if the design of compliant connecting members 225A and 225B so mandates. The use of stainless steel is preferable in the fabrication of connecting members 225A and 225B, but other biocompatible materials such as gold or titanium may be used. Springs 228A and 228B are shown in FIG. 4 as being coil-type springs.

Springs 228A and 228B thus supply a constant tension to their respective connecting wires. This tension permits implantable hearing device 10 to provide improved sound reproduction over the long term, despite aging, pressure changes, physical force, and the like. For example, in the prior art, vibrations could loosen the mechanical coupling connecting wires 25A and 25B to elements of middle ear JJ, especially over the long term. Variations in ambient pressure such as those that occur during commercial airline flights and when scuba diving also cause mechanical stress in the components of such systems, loosening their mechanical couplings. Springs 228A and 228B maintain tension, and so acceptable sound reproduction, while allowing the mechanism to compensate for such conditions.

Although the characteristics of a compliant connecting member may vary widely while still providing acceptable performance, certain materials and parameters are preferable in the design of an implantable hearing aid according to the present invention. While compliant connecting members are preferably fabricated from stainless steel, other biocompatible materials such as gold or titanium may be used, as may other materials. Certain of these materials are preferably coated with biocompatible materials (e.g., coated with gold, silicone, polyamide, titanium, or the like) by various methods (e.g., sputtering, electroplating, or the like). Such compliant connecting members may also be fabricated from strips of plastic material such as urethane or even some types of foam material. If compliant connecting member uses a spring, the spring's resonant frequency should preferably be below about 500 hertz (Hz), and most preferably below 200 Hz. For most applications, the spring should readily transmit voice frequencies (i.e., about 1500 Hz to 3500 Hz), and exhibit a flat response curve in this range. A broader frequency range may also be desirable, such as between about 500 Hz and 10,000 Hz. Normally, such a spring will exhibit a reduced response to frequencies outside these ranges. The free length of such a spring will be determined by the configuration of the hearing aid's mechanism and the subject's middle ear volume, among other factors.

Figure 5:
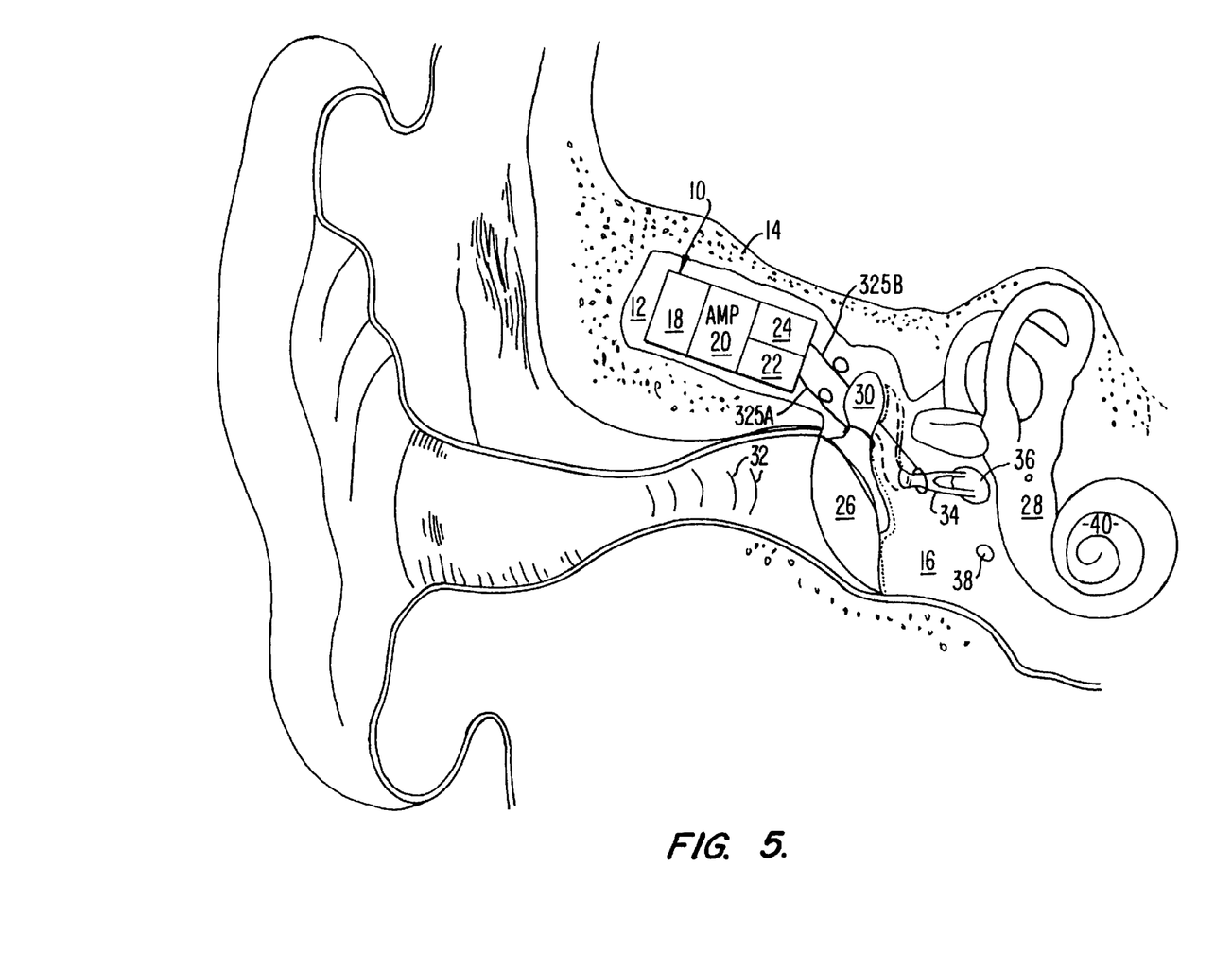
FIG. 5 is a schematic section through a portion of the skull of a human subject an implantable hearing aid according to another embodiment of the present invention.

FIG. 5 illustrates another possible configuration using compliant connecting members 325A and 325B. Compliant connecting members 325A and 325B employ a loop-type spring. Again, compliant connecting members 325A and 325B provide the tension necessary to permit the transmission of normal sound pressure levels (SPLs) to stapes 34. For normal sound pressure-induced modes to be harnessed by the tympanic membrane and transferred to input transducer 22, the maintenance of such tension is important. A tympanic membrane such as tympanic membrane 26 which is not dampened or is poorly dampened will face an increased probability of delivering erratic or distorted mechanical stimuli to input transducer 22. By providing a tensioning device such as compliant connecting member 325A, such problems are avoided.

Figure 6A:
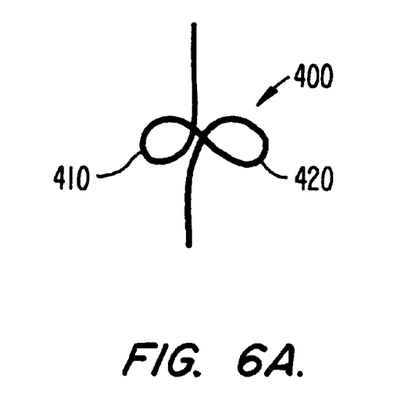
FIGS. 6A and 6B show compliant connecting members according to one embodiment of the present invention.
Figure 6B:
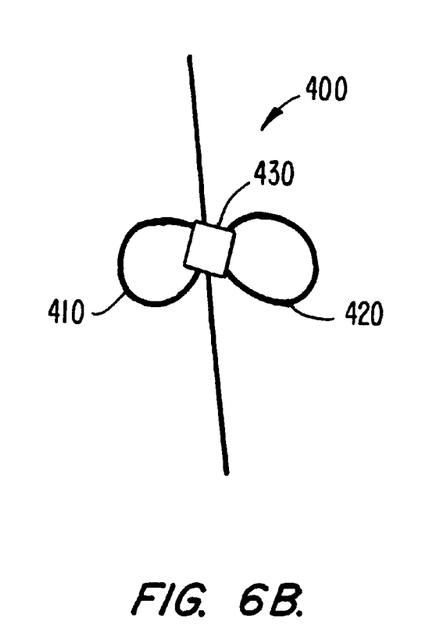

Several other types of compliant devices may serve as compliant connecting members in the present invention. FIGS. 6A and 6B illustrate bow-tie spring designs which may be employed in the present invention. A bow-tie spring 400 is shown in FIG. 6A and includes a first loop 410 and a second loop 420. Bow-tie spring 400 is shown in FIG. 6B with the addition of a sleeve 430 coupling loop 410 and loop 420. A urethane strip could also serve as a compliant connecting member. Such a strip could be attached to a respective transducer and auditory component by stainless steel wires, for example. The use of other such materials and designs will be obvious to those skilled in the art.

Figure 6C:
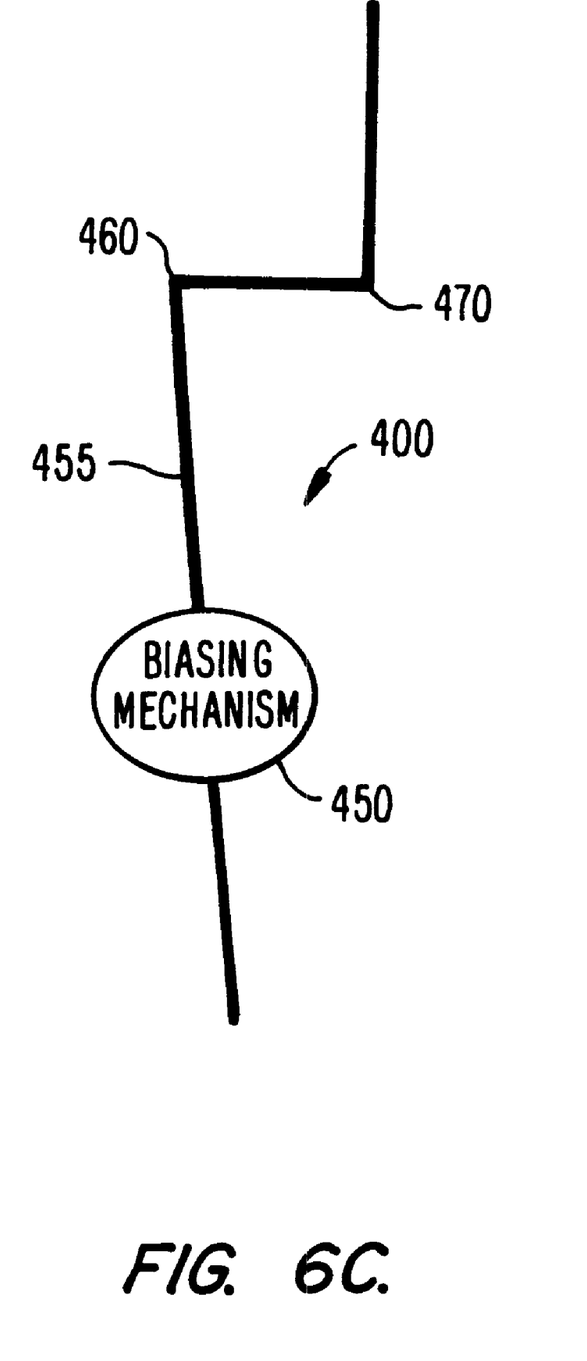
FIG. 6C shows a compliant connecting member according to yet another embodiment of the present invention.

FIG. 6C illustrates a compliant connecting member 400 with a bended segment, configured to provide a surgeon with an improved view of the surgical field during implantation. Most implantable devices are imbedded in the mastoid bone and tend to block or obscure a portion of the surgical field during system implantation. Preferably, a set of dual right-angle bends 460, 470 are added to compliant connecting member wire 455. The bended feature of compliant member wire 455 is meant to be used with any of the several types of biasing mechanisms 450 described herein, but is not so limited. The bent compliant connecting wire makes it possible for the surgeon to maneuver the implantable device out of the surgical field of view, while reducing disturbance to both the placement and the attachment of the compliant member to components of the inner ear.

However, the compliant connecting member of the present invention need not be restricted to providing tensive force between implantable hearing device 10 and structures of the inner ear. The present invention may also employ spring designs which provide compressive force. For example, the compliant connecting members shown in FIGS. 7 and 8 are capable of providing either compressive or tensive force in connecting implantable hearing device 10 (or other such device) to the ear's structures.

Figure 7:
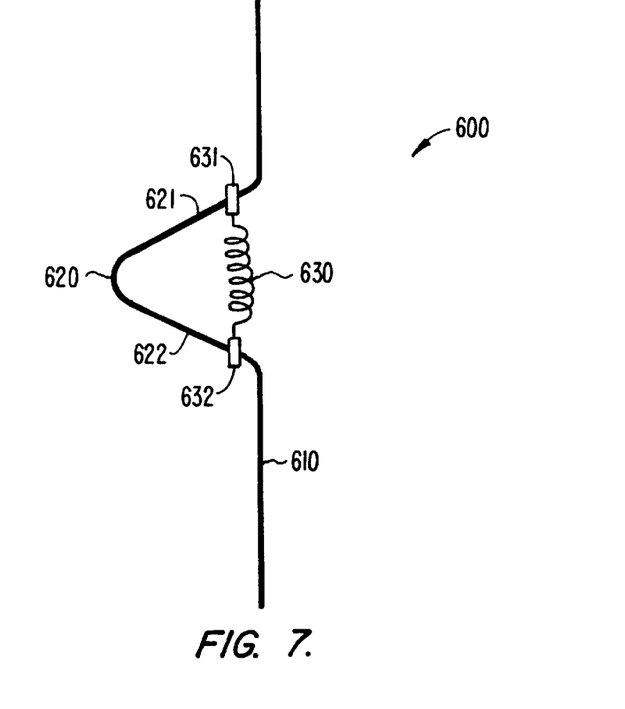
FIG. 7 shows a compliant connecting member according to yet another embodiment of the present invention.

FIG. 7 illustrates a compliant connecting member 600. Compliant connecting member 600 includes a formed wire 610 made of a material such as stainless steel and having a compressible section 620 with a first arm 621 and a second arm 622. A spring 630 is connected at a first end to arm 621 by a connector 631 and at a second end to arm 622 by a connector 632.

In operation, compliant connecting member 600 can provide either tensive or compressive force, depending on the state of spring 630. If, for the nominal length of compliant connecting member 600, spring 630 is stretched beyond its resting length, spring 630 tends to force first arm 621 and second arm 622 together. In that case, compliant connecting member 600 provides tensive force. If spring 630 is compressed, spring 630 tends to force first arm 621 and second arm 622 apart, with compliant connecting member 600 thus providing compressive force.

Figure 8:
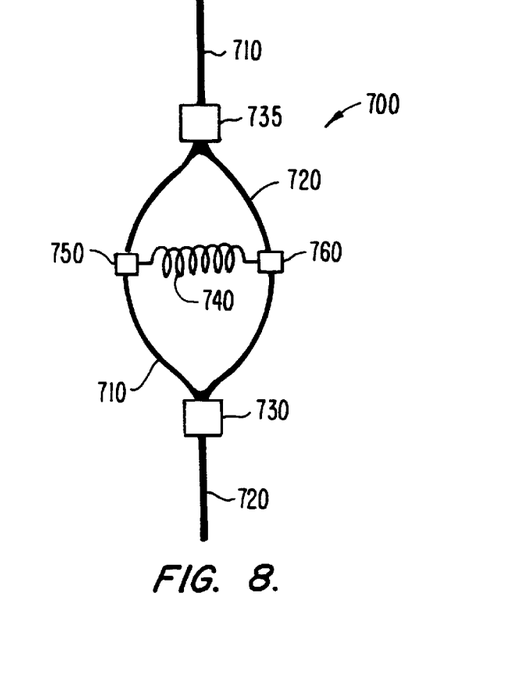
FIG. 8 shows a compliant connecting member according to yet another embodiment of the present invention

FIG. 8 illustrates yet another compliant connecting member 700 which includes a first wire 710 and a second wire 720. First wire 710 is connected at a first end to a point on second wire 720 by a coupling 730. Similarly, second wire 720 is connected at a first end to a point on first wire 710 by a coupling 735. A spring 740 is connected at a first end to a point on first wire 710 midway between couplings 730 and 735 by a coupling 750. Similarly, spring 740 is connected at a second end to second wire 720 at a point midway between couplings 730 and 735 by a coupling 760.

Compliant connecting member 700 is also capable of providing either tensive or compressive force. In a manner similar to compliant connecting member 600, this depends on the state of spring 740. If, for the nominal length of compliant connecting member 700, spring 740 is stretched beyond its resting length, spring 740 tends to force first wire 710 and second wire 720 together. In that case, compliant connecting member 700 provides compressive force. If spring 740 is compressed, spring 740 tends to force first wire 710 and second wire 720 apart, with compliant connecting member 700 thus providing a tensive force.

The present invention is not limited to being used with an implantable hearing device such as implantable hearing device 10. For example, implantable hearing devices, such as those shown in FIGS. 9, 10A–B and 11A–B, and described herein below, can also benefit from the present invention.

Figure 9:
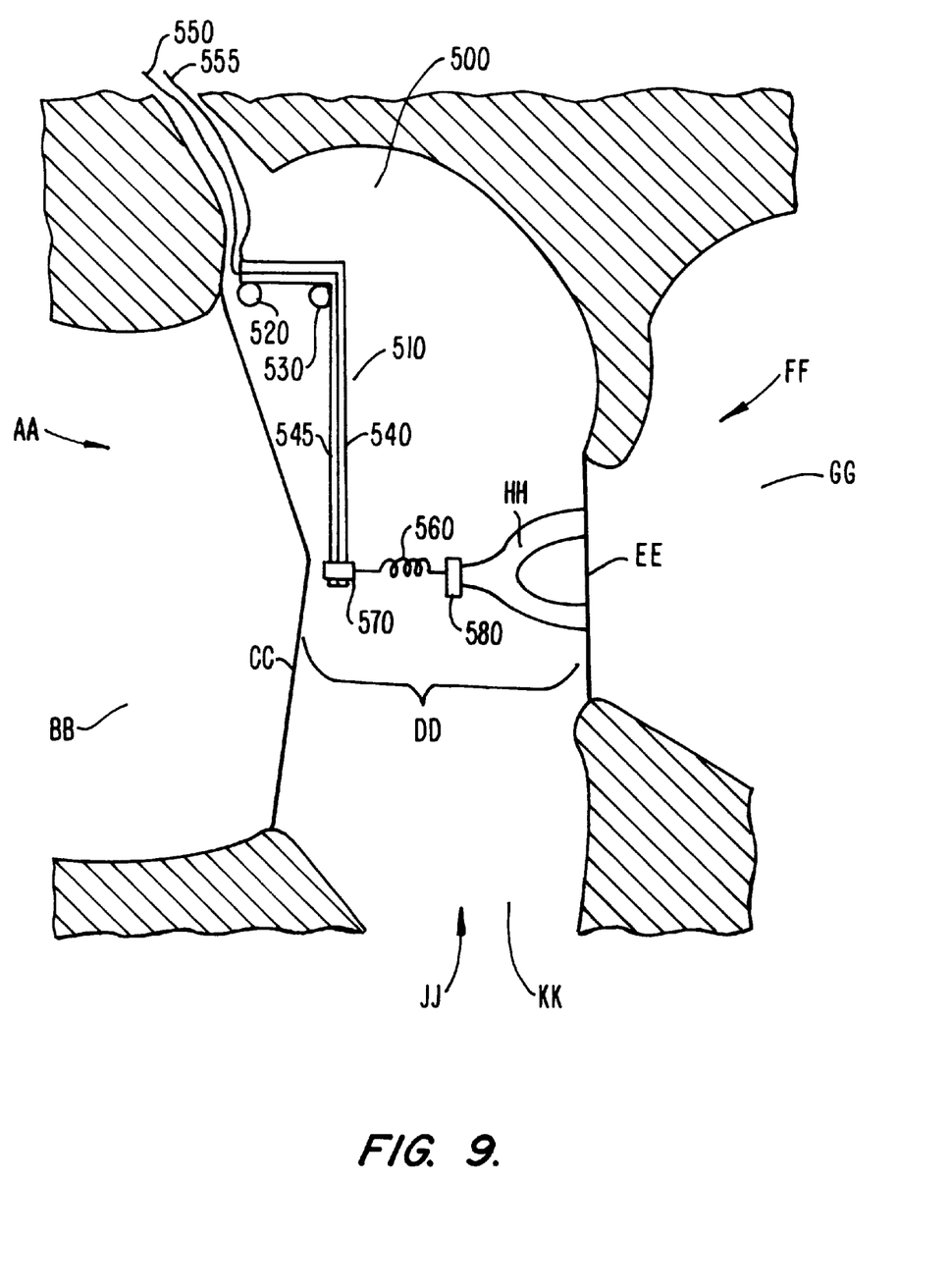
FIG. 9 is a schematic section through a portion of the skull of a human subject an implantable hearing aid according to yet another embodiment of the present invention.

In FIG. 9, an implantable hearing device 500 employs a lever arrangement capable of actuating oval window EE, or one or more of ossicles DD (e.g., stapes HH). A bimorphic lever 510 is connected to the mastoid bone of a subject's skull by anchor pins 520 and 530. Bimorphic lever 510 is preferably fabricated from two different piezoelectric materials, shown in FIG. 9 as piezoelectric strips 540 and 545. Piezoelectric strips 540 and 545 are connected, at a first end of each, to an amplifier (not shown) by wires 550 and 555.

In operation, piezoelectric strips 540 and 545 expand and contract different amounts upon the application of a given signal voltage. Thus, in a manner similar to the bimorphic strips used in thermostats, bimorphic lever 510 bends in response to the signals applied to piezoelectric strips 540 and 545. In this way, the motion of a distal end of bimorphic lever 510 (i.e., a second end of each of piezoelectric strips 540 and 545) is substantially proportional to the signal applied to piezoelectric strips 540 and 545 by the amplifier. The amplifier may take as its input electronic signals from a sound pickup (also not shown). The sound pickup receives ambient sounds and provides them to the amplifier by way of an electromagnetic coupling, for example. (Other alternatives such as directly wiring the sound pickup to the amplifier are, of course, also available.) However, if a simple wire is used to connect the distal end of bimorphic lever 510 to stapes HH, the design can be expected to suffer the previously-mentioned infirmities.

To address such limitations, a compliant connecting member 560 according to the present invention is used to couple the distal end of bimorphic lever 510 to stapes HH. Alternatively, compliant connecting member 560 could be attached directly to oval window EE. A mechanical coupling 570 attaches compliant connecting member 560 to the distal end of bimorphic lever 510. A mechanical coupling 580 attaches compliant connecting member 560 to stapes HH. As before, the benefits of the present invention are provided, including compensation for loosening of mechanical couplings 570 and 580, and other phenomena which may impair coupling between the distal end of bimorphic lever 510 and stapes HH.

Figure 10A:
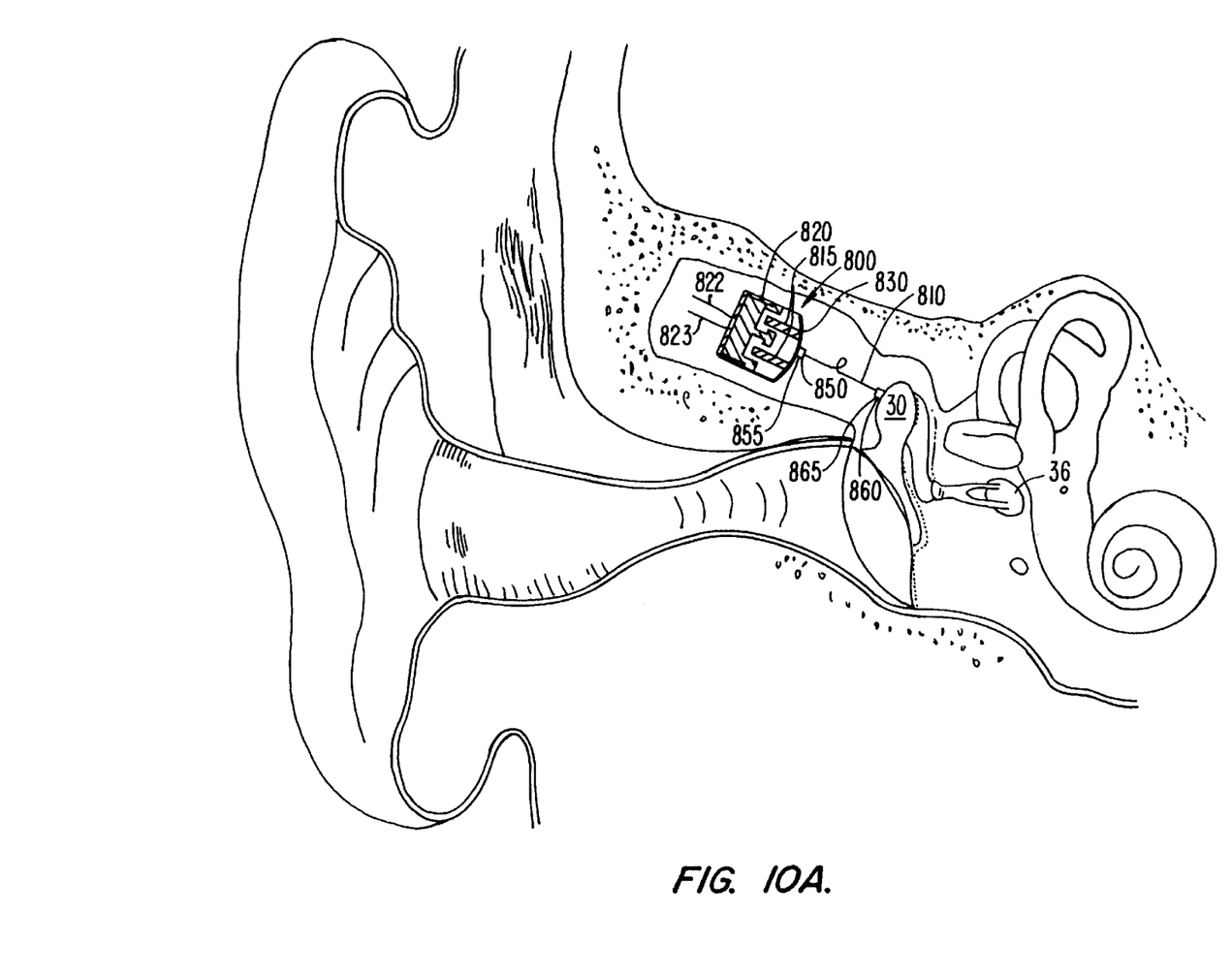
FIG. 10A is a schematic section through a portion of the skull of a human subject an electromagnetic implantable hearing aid according to yet another embodiment of the present invention.

In FIG. 10A, an implantable hearing device 800 is shown which employs an electromagnetic drive unit 820 capable of imparting vibrational energy typically through a rigid connection to one or more ossicles of the inner ear. Electromagnetic drive unit 820 is a conventional drive unit having an internal set of magnets 815 coupled to diaphragm 830. Magnets 815 are induced into motion which corresponds to a signal applied to drive unit 820. The motion of magnets 815 causes diaphragm 830 to vibrate, which drives a rigid rod connected to one or more of the bones of the inner ear.

Figure 10B:
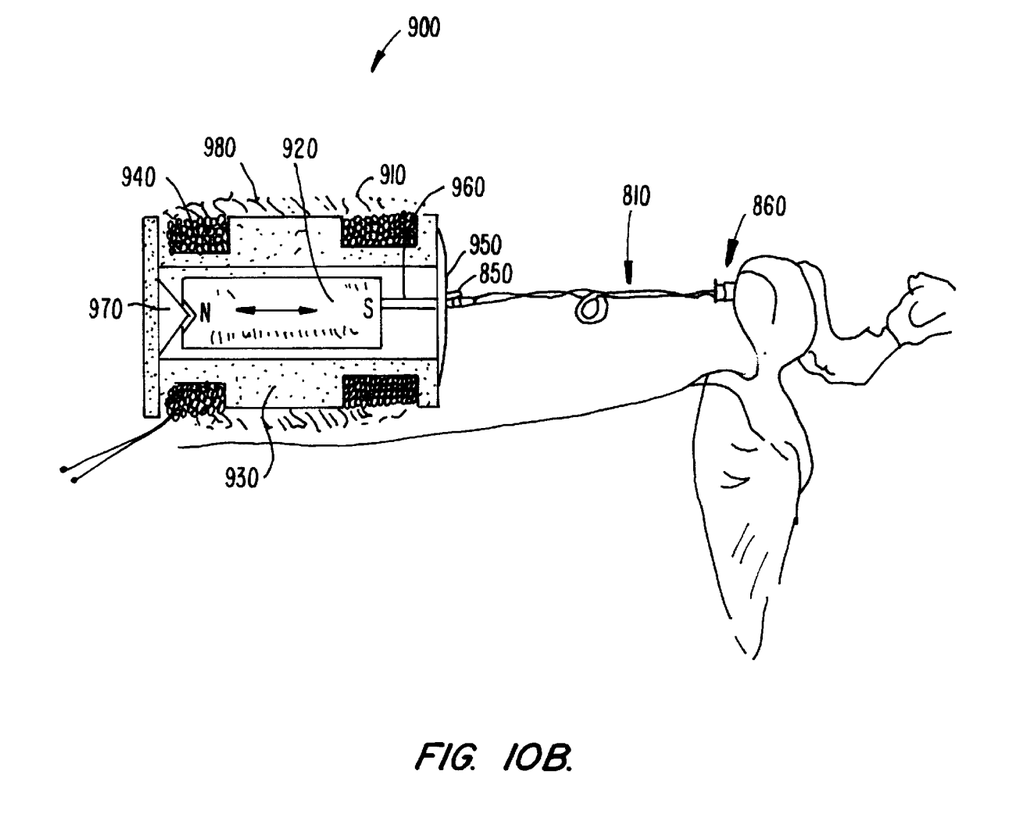
FIG. 10B is a schematic section through a portion of the skull of a human subject an improved coil floating mass electromagnetic implantable hearing aid according to yet another embodiment of the present invention.

In an alternative device, shown in FIG. 10B, the implantable hearing device 900 is an improved coil floating mass unit. Floating mass drive unit 910 is typically rigidly connected to one or more of the inner ear ossicles and is designed to be hermetically encapsulated. The encapsulation isolates key components of the unit to ensure long term stability and performance of the implant. Floating mass electromagnetic drive unit 910 has a mass, typically a magnet 920, disposed within hermetically sealed housing 930. Preferably housing 930 is made of titanium or other biocompatible material. Coils 940 made of, for example, gold, are wrapped on the outside of housing 930 and add strength and protection to the housing, among other things. Protective coating 980 is also disposed on the outside of the housing to provide strength and protection, as well. Diaphragm 950, preferably made of titanium and laser welded to housing 930, is in contact with one end of internal magnet 920 through connecting member 960. On the end of housing 930 opposed to diaphragm 950 is a spring mechanism 970 coupled to another end of magnet 920 and suspends magnet 920, allowing it to float within housing 930. The motion of magnet 920 is induced by a current traveling through coils 940. The resonance of the system is tuned by adjusting the durometers and/or vibratory parameters of silicone spring 970, diaphragm 950, and connecting member 960 (as a system or individually). Ideally, electromagnetic unit 910 resonates at around 1500 Hz to mimic the vibratory motion of a human ear.

In either of the above described electromagnetic driver designs 820 or 910, the diaphragm is made to vibrate upon application of a given input signal in a manner similar to an acoustic speaker. In this way, the motion of the diaphragm is proportional to the signal applied to the electromagnetic unit. The rigid connection of the hearing device to the inner ear is made using a strut of a rigid material in the interest of accurately transmitting mechanical vibrations to the ossicles and faithfully reproducing sound waves. However, by using a rigid strut to connect the diaphragm to one or more bones of the inner ear, the driver designs 820 and 910 can be expected to suffer the previously mentioned weaknesses.

To address such weaknesses, a compliant connecting member according to the present invention is used with either electromagnetic device described above. For example, FIG. 10A shows compliant member 810, according to the present invention, being used to couple diaphragm 810 to malleus 30. Alternatively, compliant connecting member 810 could be attached directly to any of the other bones of the middle ear. Moreover, FIG. 10B shows the floating mass electromagnetic unit being similarly connected to an ossicle bone using the compliant member of the present invention.

In a preferred embodiment, magnetic coupling devices are used to attach the compliant connecting member to the diaphragm and to the ossicle bones. As shown in FIG. 10A, for example, single magnets 855, 865 are coupled on to diaphragm 830 and target ossicle bone 30, respectively. Single magnets 850, 860, having an opposing charge are coupled to the ends of compliant member 810. To secure compliant member 830 into the system, the magnets are brought into contact and hold member 810 in place. As before, the benefits of the present invention are provided, including holding the tensioning unit in its proper location, facilitating surgical placement, rendering the device reversible and other phenomena which may impair coupling between the diaphragm and the compliant member and the compliant member and the bones of the inner ear.

Figure 11A:
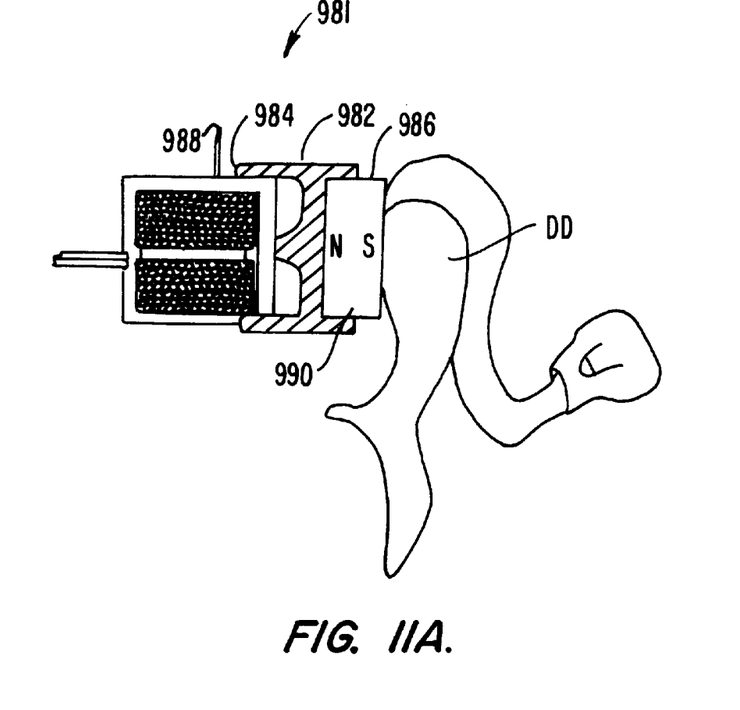
FIGS. 11A–B are schematic sections through a portion of the skull of a human subject a coil electromagnetic implantable hearing aid according to yet another embodiment of the present invention.

Another potential implantable hearing device, as shown in FIG. 11A, is a coil-magnet implantable device. FIG. 11A illustrates an embodiment of the present invention used with the coil-magnet configuration. Coil-magnet device 981 has a coil 988 in a housing and is brought into close proximity with magnet 986, which is coupled to on one or more ossicle bones of the inner DD. When coil 988 is energized, motion is induced in magnet 986. Compliant member 982 provides a compliant connection between coil device 988 and magnet 986. Preferably the compliant member is a keeper/spring 982, as shown in FIG. 11A, and is made from a soft pliable material, such as silicone or rubber. Keeper/spring 982 has a first open end 984 adapted to receive coil device 988. The second open end 986 is adapted to receive magnet 986 and center the magnet's position with coil device 988. The motion of magnet 986 is proportional to the signal applied to coil device 988. The compliant connection of coil device 988 to the inner ear is made to accurately transmit mechanical vibrations to the ossicles and faithfully reproduce sound waves. The compliant member or keeper/spring 982 is further designed to tune the resonance of the system and ease the method of implantation of the coil device. To ease the implantation process, magnet 986, with keeper/spring 982 coupled to one side, is coupled to a bone of the inner ear. After magnet 986 is secured in position, coil device 988 is moved into position and coupled to compliant keeper/spring 982.

Figure 11B:
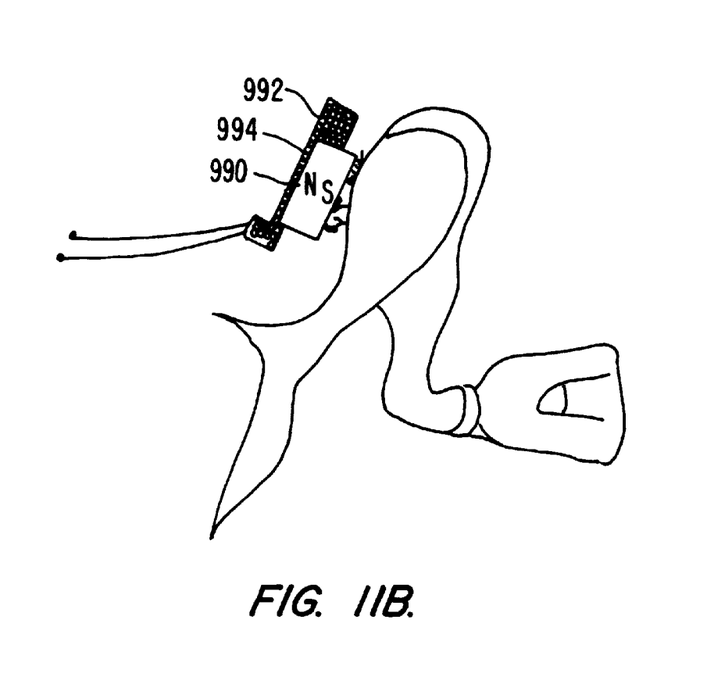

FIG. 11B, illustrates yet another embodiment of the present invention. Compliant member 994 is coupled on a perimeter of magnet 990 and resembles a gasket. Coil 992 is then positioned to surround the portion of magnet 990 having the gasket-like compliant member 994 disposed thereon.

It is to be understood that the above description is intended to be illustrative and not restrictive. Many embodiments will be apparent to those of skill in the art upon reviewing the above description. By way of example, the inventions herein have been illustrated primarily with regard to the type of implantable hearing devices shown in Schaefer, as well as others, but they are not so limited. Those skilled in the art will recognize other equivalent or alternative methods of maintaining tension in the mechanical couplings of an implantable hearing device while remaining within the scope of the claims of the present invention. Although the above description discusses the use of stainless steel in particular, other materials may be used for the compliant connecting members of the present invention. The scope of the invention should, therefore, be determined not with reference to the above description, but should instead be determined with reference to the appended claims, along with the full scope of equivalents to which such claims are entitled.

What is claimed is:

1. An implantable hearing device comprising:
   a transducer which produces vibrations in response to an electrical signal; and
   a connecting member having a first end connected to the transducer and a second end adapted to connect to a component of a human ear, wherein the transducer and the component of a human ear are elastically coupled by the connecting member;
   wherein said connecting member comprises a resilient biasing mechanism having a resonant frequency below about 500 hertz.

2. The apparatus of claim 1, wherein said resilient biasing mechanism has a resonant frequency below about 200 hertz.

3. An implantable hearing device, which is coupled between a tympanic membrane and an oval window of an ear of a human subject, comprising:
   an amplifier;
   a first transducer electrically coupled to said amplifier for converting mechanical vibrations to electrical signals;
   a second transducer electrically coupled to said amplifier for converting electrical signals to mechanical vibrations;
   a first connecting member having a first end connected to the first transducer and a second end adapted to connect to the tympanic membrane, wherein said first transducer and said tympanic membrane are elastically coupled by said first connecting member; and
   a second connecting member having a first end connected to said second transducer and a second end adapted to connect to said oval window, wherein said second transducer and said oval window are elastically coupled by said second connecting member;
   wherein said first and second connecting members each comprise a resilient biasing mechanism having a resonant frequency below about 500 hertz.

4. The apparatus of claim 3, wherein said first connecting member creates a tensive force between the tympanic membrane to said first transducer when coupled therebetween.

5. The apparatus of claim 3, wherein said second connecting member creates a tensive force between said second transducer to the oval window when coupled therebetween.

6. An implantable hearing device adapted to connect to a component of an ear of a human subject, comprising:
   a hearing device for improving hearing of the human subject; and
   a resilient biasing mechanism for elastically coupling said hearing device to the component of the ear, said resilient biasing mechanism having a resonant frequency below about 500 hertz.

7. The apparatus of claim 6, wherein said resilient biasing mechanism for elastically coupling creates a tensive force between said implantable hearing device and the component of the ear.

8. A method of improving hearing in a human subject comprising:
   implanting an implantable hearing device into a mastoid bone of the human subject; and
   elastically coupling said implantable hearing device to a vibratory component of the ear using a connecting member, said connecting member comprising a resilient biasing mechanism having a resonant frequency below about 500 hertz.

9. A method of improving hearing in a human subject, an ear of the human subject having a tympanic membrane and an oval window, comprising:
   implanting an implantable hearing device in a mastoid bone of the human subject, said implantable hearing device comprising
   (a) an amplifier,
   (b) a first transducer electrically coupled to said amplifier, and
   (c) a second transducer electrically coupled to said amplifier;
   elastically coupling the tympanic membrane and said first transducer using a first compliant connecting member; and
   elastically coupling said second transducer and the oval window using a second compliant connecting member;
   wherein said first and second connecting members each comprise a resilient biasing mechanism having a resonant frequency below about 500 hertz.

10. In an implantable hearing device of the type coupled to a component of an ear of a human subject, the improvement comprising:
    a connecting member adapted to elastically couple the implantable hearing device to the component of the ear, said connecting member comprising a resilient biasing mechanism having a resonant frequency below about 500 hertz.

11. In an implantable hearing device adapted to be coupled between a tympanic membrane and an oval window of an ear of a human subject and having an amplifier, a first transducer electrically coupled to the amplifier, and a second transducer electrically coupled to the amplifier, the improvement comprising:
   a first connecting member adapted to elastically couple the tympanic membrane to said first transducer; and
   a second connecting member adapted to elastically couple said second transducer to the oval window;
   wherein said first and second connecting members each comprise a resilient biasing mechanism having a resonant frequency below about 500 hertz.

12. In an implantable hearing device adapted to being coupled to a component of the middle ear of a human subject, comprising an electromagnetic unit having a diaphragm, the improvement comprising:
   a connecting member adapted to elastically couple a component of the middle ear to said diaphragm.

13. The improved hearing device of claim 12, wherein the connecting member is adapted to be coupled to the diaphragm and the structure of the middle ear using magnetism.

14. The improved hearing device of claim 12, wherein the implantable device is hermetically sealed.

15. An implantable hearing device of the type coupled to one or more ossicles of an inner ear of a human subject, comprising:
   a housing;
   an electromagnetic unit having a magnet disposed inside said housing and a coil surrounding a portion of said housing;
   a diaphragm mechanically coupled to said electromagnetic unit, wherein motion of the diaphragm is proportional to a signal applied to said electromagnetic unit; and
   a connecting member adapted to elastically couple said diaphragm to the one or more ossicles of the human ear.

16. The improved hearing device of claim 15, wherein the implantable hearing device is hermetically sealed.

17. A method of improving hearing in a human subject, an ear of the human subject having a middle ear structure, comprising:
   implanting an implantable hearing device in a mastoid bone of the human subject, said implantable hearing device comprising:
      an electromagnetic unit having a diaphragm mechanically driven by said electromagnetic unit; and
   elastically coupling said diaphragm and a component of the middle ear structure using a first connecting member.

18. The method of claim 17, wherein the implantable hearing device is hermetically sealed.

19. An implantable hearing device adapted to being coupled to one or more ossicles of an inner ear of a human subject, comprising:
   a coil;
   a compliant connecting member adapted to elastically couple said coil to a magnet, the magnet being coupled to the one or more ossicles of the human ear.

20. The hearing device of claim 19, wherein the compliant connecting member comprises a keeper/spring device.

21. A method of improving hearing in a human subject, an ear of the human subject having a middle ear structure, comprising:
   implanting a magnet on a component of the middle ear structure;
   elastically coupling the magnet to a first portion of a connecting member; and
   elastically coupling a coil device to a second portion of said connecting member.

22. The method of claim 21, wherein the connecting member comprises a keeper/spring device.

23. An implantable hearing device comprising:
   a transducer which produces vibrations in response to an electrical signal; and
   a connecting member having a first end connected to the transducer and a second end adapted to connect to a component of a human ear, wherein the transducer and the component of a human ear are elastically coupled by the connecting member;
   wherein said connecting member comprises a urethane strip.

24. An implantable hearing device, which is coupled between a tympanic membrane and an oval window of an ear of a human subject, comprising:
   an amplifier;
   a first transducer electrically coupled to said amplifier for converting mechanical vibrations to electrical signals;
   a second transducer electrically coupled to said amplifier for converting electrical signals to mechanical vibrations;
   a first connecting member having a first end connected to the first transducer and a second end adapted to connect to the tympanic membrane, wherein said first transducer and said tympanic membrane are elastically coupled by said first connecting member; and
   a second connecting member having a first end connected to said second transducer and a second end adapted to connect to said oval window, wherein said second transducer and said oval window are elastically coupled by said second connecting member;
   wherein said first and said second connecting members each comprise a urethane strip.

25. An implantable hearing device, which is coupled between a tympanic membrane and an oval window of an ear of a human subject, comprising:
   an amplifier;
   a first transducer electrically coupled to said amplifier for converting mechanical vibrations to electrical signals;
   a second transducer electrically coupled to said amplifier for converting electrical signals to mechanical vibrations;
   a first connecting member having a first end connected to the first transducer and a second end adapted to connect to the tympanic membrane, wherein said first transducer and said tympanic membrane are elastically coupled by said first connecting member; and
   a second connecting member having a first end connected to said second transducer and a second end adapted to connect to said oval window, wherein said second transducer and said oval window are elastically coupled by said second connecting member;
   wherein said first and said second connecting members each comprise at least one set of angled bends.

26. An implantable hearing device adapted to connect to a component of an ear of a human subject, comprising:
   a hearing device for improving hearing of the human subject; and
   means for elastically coupling said hearing device to the component of the ear;
   wherein said means comprises a urethane strip.

* * * * *